(12) United States Patent
Devonec (10) Patent No.: US 9,517,120 B2
(45) Date of Patent: Dec. 13, 2016

(54) DEVICE FOR POSITIONING A STENT

(76) Inventor: Marian Devonec, Miribel (FR)

( * ) Notice: Subject to any disclaimer, the term of this patent is extended or adjusted under 35 U.S.C. 154(b) by 1046 days.

(21) Appl. No.: 12/451,068

(22) PCT Filed: May 16, 2008

(86) PCT No.: PCT/IB2008/002471
§ 371 (c)(1),
(2), (4) Date: Dec. 28, 2009

(87) PCT Pub. No.: WO2008/155672
PCT Pub. Date: Dec. 24, 2008

(65) Prior Publication Data
US 2010/0121341 A1    May 13, 2010

Related U.S. Application Data

(60) Provisional application No. 60/924,476, filed on May 16, 2007.

(51) Int. Cl.
*A61F 2/04* (2013.01)
*A61F 2/94* (2013.01)
*A61F 2/95* (2013.01)

(52) U.S. Cl.
CPC .. *A61F 2/04* (2013.01); *A61F 2/94* (2013.01); *A61F 2/95* (2013.01); *A61F 2002/047* (2013.01); *A61F 2002/048* (2013.01)

(58) Field of Classification Search
CPC .. A61F 2/04; A61F 2002/047; A61F 2002/04; A61M 27/008
USPC ................. 623/1.11, 23.7; 604/525; 600/585
See application file for complete search history.

(56) References Cited

U.S. PATENT DOCUMENTS

| | | | |
|---|---|---|---|
| 5,518,498 A * | 5/1996 | Lindenberg et al. | ............ 600/30 |
| 5,797,929 A * | 8/1998 | Andreas et al. | ............. 606/148 |
| 5,876,417 A | 3/1999 | Devonec et al. | |
| 6,290,666 B1 * | 9/2001 | Devonec | ..................... 623/1.16 |
| 6,494,879 B2 * | 12/2002 | Lennox et al. | ..................... 606/8 |
| 2003/0083643 A1* | 5/2003 | Wilson et al. | ................ 604/523 |
| 2004/0167437 A1* | 8/2004 | Sharrow et al. | ............. 600/585 |
| 2004/0193283 A1 | 9/2004 | Rioux et al. | |

FOREIGN PATENT DOCUMENTS

WO    WO 00/78246 A2    12/2000
WO    WO 2006/126060 A2    11/2006

OTHER PUBLICATIONS

International Preliminary Report on Patentability issued in International Application No. PCT/IB2008/002471 on Nov. 17, 2009.
International Search Report issued on Jan. 27, 2009 in International Application No. PCT/IB2008/002471.

* cited by examiner

*Primary Examiner* — Diane Yabut
(74) *Attorney, Agent, or Firm* — Oliff PLC (57) ABSTRACT

A device for positioning a stent in a natural canal after passing through an obstacle at the level of a target organ. The device includes a stent, a pusher tube, and a guide. The guide is configured to push the stent through the lumen of the natural canal, and includes at least one flexible part having a predetermined longitudinal stiffness and a lateral flexibility that allow a reversible deformation from a straight position to a bent position so as to follow the curve of the natural canal under the application of minimal external forces exerted by an operator. The device is particularly adapted to the technical field of urology.

17 Claims, 4 Drawing Sheets

DEVICE FOR POSITIONING A STENT

The present invention concerns a device for positioning a stent in a natural canal after the passage through an obstacle at the level of a target organ. The obstacle can consist in a sphincter.

The present invention is particularly adapted to the technical field of urology, in which an endo-urethral stent has to be inserted into the bladder after the passage through the urinary striated sphincter along the male urethra, in order to suppress the obstruction in the area of the prostatic urethra and to allow the flowing of the urine from the bladder through at least one orifice laterally positioned at a distal tip of the said stent.

However, the device according to the invention could obviously be used to allow the insertion of a stent in a lumen of a natural canal of another target organ.

The insertion of a stent in a lumen of a natural canal must be carefully carried out without causing any injury by the passage through the said canal. Furthermore, it is important to be sure that the stent is correctly positioned at the level of the concerned organ.

For these reasons, the correct positioning of a stent requires usually the use of visual control. For example, correct positioning of endo-urethral stents above (Memokath) or on both sides (Prostacoil) of the striated sphincter muscle is controlled via endoscopy, fluoroscopy or trans-rectal ultrasound.

In the technical field of endo-urethral stents, the tactile feed-back of the abutment of a part of the device allowing its insertion against the external sphincter was proposed as a means for correct positioning to avoid the use of any instrumentation during the insertion of a stent.

More precisely, the U.S. Pat. No. 5,876,417 discloses two distinct embodiments of a device allowing the insertion of an endo-urethral stent thanks to a tactile feed-back of the operator during the insertion, said device comprising:
- a tube assembly being the prostatic stent,
- an insertion device slidably receivable into said tube assembly,
- an expandable member operative to move between an expanded state wherein the expandable member expands radially outwardly and abuts against the sphincter and a collapsed state wherein the expandable member collapses,
- expansion and/or collapse controlling means of said expandable member.

According to the first embodiment, the expandable member is an inflatable balloon localized on the outer surface of the proximal tube section.

According to the second embodiment, the expandable member is a Malecot arrangement comprising tongues, each tongue being foldable between two positions, namely a first position folded outwards at its centre and an unfolded position in which it is included in the wall of the rod of the insertion device.

The patent application WO 2006/126060 A2 discloses a third embodiment in which the expandable member in the shape of tongues of the half-Malecot portion disposed on the proximal tube section is arranged to abut permanently in said expanded state against the urinary striated sphincter and to oppose any upward movement in the urethra of the catheter apparatus.

These three embodiments fail to regularly reproduce correct positioning of the stent on both sides of the striated sphincter, i.e. the upper tube in the prostatic urethra with its tip in the bladder and the lower tube in the bulbous urethra and the flexible connection between the two tubes through the sphincter. Often, the lower tubular element of the stent is pushed too above the sphincter and the stent is released too far inside the bladder. Indeed, the abutment of the inflated balloon of the first embodiment, or of the tongues of the Malecot of the second embodiment, or of the tongues of the half-Malecot of the lower tubular element of the third embodiment against the striated sphincter is not clearly perceived by the operator. After removal, the stent has to be reinserted and positioned under the control of endoscopy or trans-rectal ultra-sonography.

The present invention remedies the disadvantages associated with the known systems described hereinabove by providing a device allowing the insertion of a stent in a lumen of a natural canal at the level of a target organ, after the passage through an obstacle, such as a sphincter, using tactile feed-back, which is perceived by the operator thanks to a deformation of the device by the passage through the said obstacle and by a significant change in the direction of said canal.

Indeed, the deformation of the device consists in a significant change in the direction following the passage through the obstacle which creates a significant increasing of the resistance to progression of the device inside the lumen of the natural canal which is suddenly felt by the operator. So, the progression of the device cannot continue unless the operator applies to the device a force that will more deform the canal. Furthermore, the deformation of the device to pass through the obstacle can be obtained under the application of minimal external forces, which is particularly advantageous, because it prevents from any injury at the level of the natural canal.

Thus, according to the present invention, it is possible to apply a therapeutic procedure, i.e. the insertion of a stent, at the level of a target organ located at a known distance from a so localized anatomical obstacle, which can consist in a sphincter.

Thus, the device according to the invention can be used for instance in the field of urology to the localization of the striated sphincter along the male urethra or in the field of gastro-enterology to the localization of Oddi's sphincter. These are non limitative applications. In both cases, the sphincter is located at the summit of the angle formed by the two portions of a natural canal on each side of the sphincter.

The following description will more focus on the case of the striated sphincter of the male urethra in order to deliver a stent above the striated sphincter inside the prostatic urethra. Indeed, in this case, the aim of the stent is to relieve the obstruction of the prostatic urethra related to benign prostatic hypertrophy which impairs normal urine flow.

In order to achieve the above mentioned objectives, the device according to the present invention comprises a stent, a guide and a pusher tube which will be hereafter more described.

Moreover, the above mentioned deformation of the device according to the invention is obtained thanks to a particular and innovative part of this device which is a guide and constitutes another object of the invention.

The guide according to the invention is conceived to push a stent through a lumen of a natural canal. It comprises at least one flexible part having a predetermined longitudinal stiffness and a lateral flexibility consisting in a reversible deformation from a straight position to a bent position so as to follow the curve of the natural canal under the application of minimal external forces applied by an operator.

By application of minimal external forces, it is to be understood that the insertion of the stent thanks to the device comprising the said guide does not cause any injury in the natural canal.

The longitudinal stiffness of the flexible part of the guide is predetermined such that the said guide does not kink by pushing a stent along a lumen of a natural canal.

The lateral flexibility of the flexible part consists in a reversible deformation from a straight position to a bent position by an angle, which may be comprised in a preferred embodiment of the invention between 90° or more.

The at least one flexible part of the guide may have different lateral flexibility.

So, the guide is longitudinally stiff enough to push a stent along a lumen of a natural canal without kinking and laterally flexible enough to be deformed by the passage through an obstacle which can be a sphincter followed by a significant change in direction of said canal.

In a preferred embodiment of the invention, the longitudinal stiffness of the guide is predetermined such that the guide can push an endo-urethral stent along the male urethra.

The at least one flexible part may consist in a guide wire.

The guide may include a proximal end which comprises a means of abutment. Hereafter in the following of the description, by "proximal", it is to be understood as meaning proximal to the operator.

The opposite term is "distal" which is to be understood as meaning distal to the operator.

Furthermore, the guide may comprise at least one proximal rod prolongated by the at least one flexible part. The said rod may be rigid.

So, in an embodiment of the invention, the guide may be composed of a rigid rod prolongated by a flexible part, which can be preferably a guide wire.

The guide may comprise at least two flexible parts. The flexible part closest the rod may have a higher lateral flexibility than the other flexible part(s), to facilitate the bending of the guide. This high flexibility can preferably be present on a short distance. Thus, in an embodiment of the invention, the guide may be composed of a rigid rod prolongated by a flexible part having two portions with different flexibility. More precisely, the portion of the flexible part which is closest the rigid rod may have a higher flexibility than the second portion.

In an embodiment of the invention, the flexible part of the guide can be made of a predetermined material, so that the said guide comprises different parts having different lateral flexibility.

In another embodiment of the invention, the at least one flexible part of the guide may be made of different materials, so that the flexible parts of the guide may have different lateral flexibility.

In another embodiment of the invention, the guide may comprise different flexible parts having different diameter. More preferably, the flexible part closest the rod may have a thinner diameter than the other parts of the flexible parts of the guide. In an embodiment of the invention, this flexible part with a thinner diameter may be a short portion measured from the distal end of the rod of the flexible part of the guide.

In an embodiment of the invention, the guide may include a distal tip comprising a protective means, which prevents from any injury at the level of the natural canal during the removal and/or the insertion of the guide. In an embodiment of the invention, the said protective means has a spherical shape.

Furthermore, the stent described hereafter constitutes another object of the invention.

According to the present invention, a variety of stents can be used for different target organs. In a preferred embodiment of the invention, the stent can be an endo-urethral stent.

In a favorite embodiment, the stent comprises a distal blind tip.

The stent may comprise a lateral wall, which has at least one orifice for draining a liquid (for example urine in the case of an endo-urethral stent). In a preferred embodiment of the invention, the said orifice is close to a distal tip of the stent.

In an embodiment of the invention, the stent may include a longitudinal sheath, which extends from a distal tip of the stent to rearwards the orifice, so that a distal tip of the guide can be inserted into the said sheath. Thus, it avoids that the distal tip of the guide passes through the orifice and causes any injury at the level of the natural canal. By sheath, it is to be understood that the distal tip of the guide can be correctly inserted into the said sheath without any risk of dislodgment. Thus, it ensures the correct positioning of the guide into the stent. In a preferred embodiment of the invention, the sheath has a diameter just above the diameter of the distal tip of the guide.

In another embodiment of the invention, the stent has a massive distal tip and said stent comprises a channel, said channel having a proximal part prolongated by a distal part, whose section is smaller than the section of the proximal part of the said channel. The orifice is localized laterally in the proximal part, so that the liquid can be drained in the proximal part of the said channel having the biggest section. The distal part is thin enough so that the distal tip of the guide can be correctly inserted into the said distal part without any risk of dislodgment.

According to this embodiment, the said channel ensures the correct positioning of the distal tip of the guide into the stent thanks to the distal part of the said channel. Furthermore, in a preferred embodiment of the invention, the distal part has a diameter just above the diameter of the distal tip of the guide.

The device according to the present invention is conceived for positioning a stent in a natural canal at the level of a target organ after the passage through an obstacle. The device comprises:
 a guide according to the invention,
 a stent having an internal housing in which the guide is intended to be inserted,
 a pusher tube including a proximal end which comprises a means of connection, and
 a thread having a proximal end which is blocked in the said means of connection.

The thread has a length such that the thread is blocked in a stretched position when the guide is correctly inserted into the pusher tube and the distal tip of the guide is in contact with the distal tip of the said stent.

So, when the thread is in a stretched position, it prevents from the removal of the guide.

More particularly, it may be interesting to use a stent as described above.

Moreover, when the guide includes a proximal end comprising a means of abutment, the length of the thread is such that said thread is blocked in a stretched position, once said means of abutment is direct in contact with the proximal end of the pusher tube and the distal tip of the guide is in contact with the distal tip of the said stent.

Moreover, the device according to the present invention may comprise an endo-urethral stent.

Furthermore, another object of the present invention consists in a therapeutic method for positioning a stent at the level of a target organ after the passage through an obstacle by using a device according to the invention.

The present invention is now described with reference to annexed drawing herein.

Figure 3A:
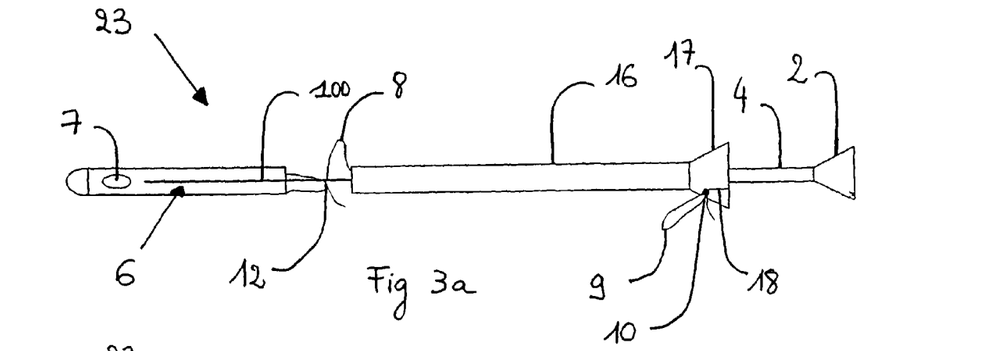
FIG. 3a shows schematically a device according to the invention in a "loose state".
Figure 3B:
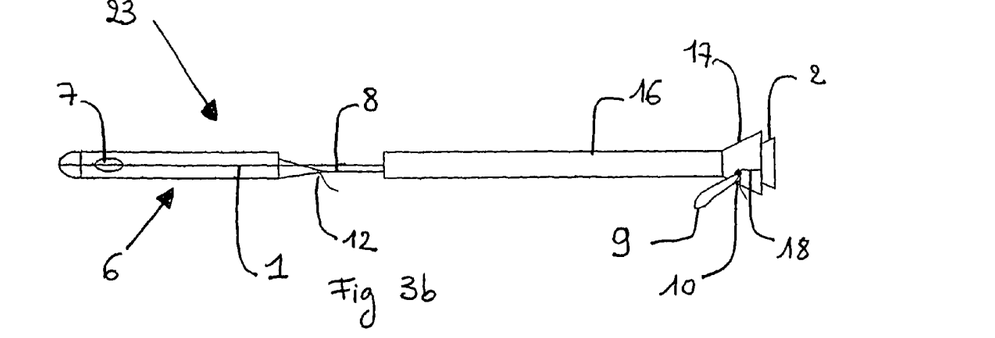
FIG. 3b shows schematically the device according to FIG. 3a in a "stretched state".

As shown in FIGS. 1a to 1d, the guide 1, 100 comprises at least one flexible part having a longitudinal stiffness and a lateral flexibility. The guide 1, 100 comprises a proximal end including a means of abutment 2. The means of abutment 2 may have a substantially conical extending shape which can be hollow or massive. Indeed, as shown in FIG. 3a and FIG. 3b, the guide 100 is inserted into a pusher tube 16 so that the means of abutment 2 of the guide 100 is in contact with the proximal end 17 of the pusher tube 16 which can have a complementary shape to the means of abutment 2.

The length of the guide 1, 100 is chosen to correspond to the length of the stent 6 plus the length of the obstacle plus the length of the pusher tube 16. The obstacle can consist in a sphincter 21.

The longitudinal stiffness of the guide 1, 100 is such that the distal tip of the guide 1, 100 is stiff enough to push forwards the blind tip of the stent 6 through the lumen of the natural canal, which can be the male urethra 22 in the case of an endo-urethral stent, i.e., push the stent 6 through the naturally closed striated sphincter 21 and through the obstructed prostatic urethra, without kinking.

The lateral flexibility of the guide 1, 100 consists in a reversible deformation, preferably by an angle of 90 degrees or more from a straight position (i.e. "still state") (FIGS. 1a to 1c) to a bent position (i.e. "bent state") (FIG. 1d) under the application of minimal external forces exerted by an operator.

Figure 1A:
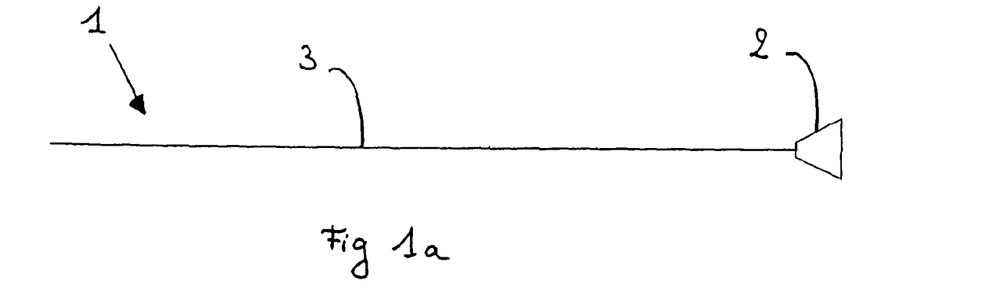
FIGS. 1a to 1c show schematically three different embodiments of a guide according to the present invention in a "still state".
Figure 1B:
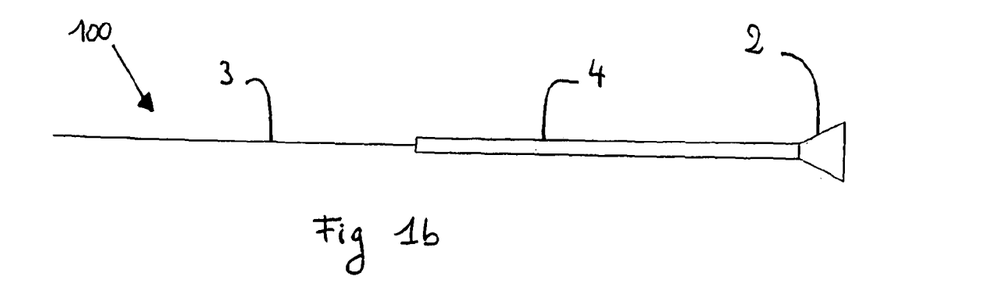
Figure 1C:
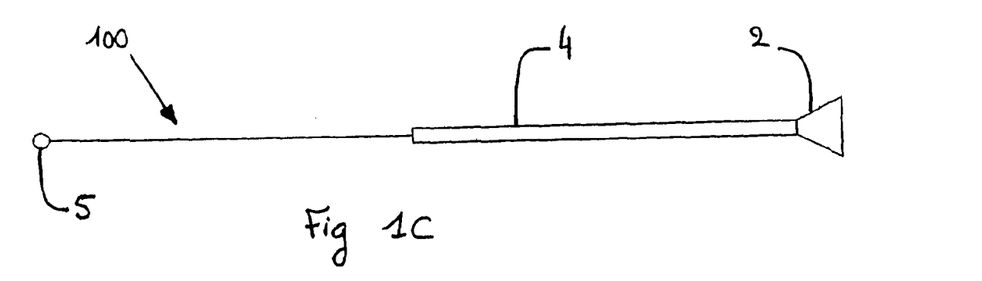
Figure 1D:
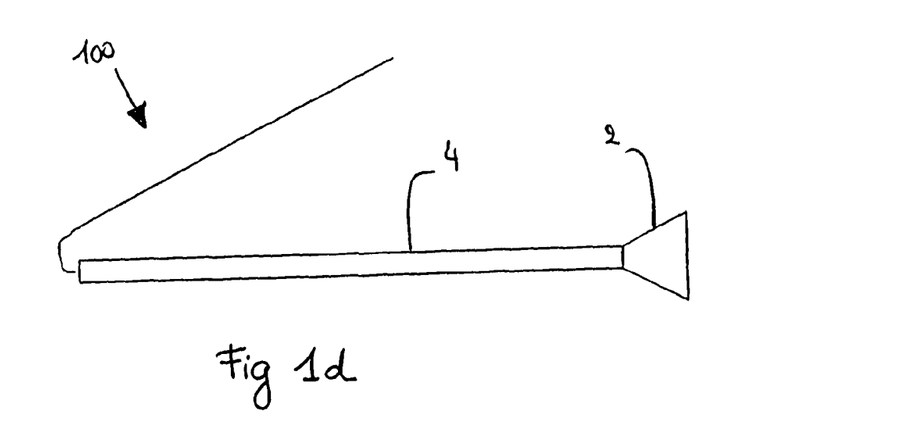
FIG. 1d corresponds to the guide showed in FIG. 1b in a "bent state".

As shown in FIG. 1d, the guide 100 can be bent at a distal end of the rod 4. In an embodiment of the invention, the lateral flexibility of the guide wire 3 can be particularly high on a short distance, preferably one centimeter measured from the distal end of the rod 4, and so to facilitate the bending of the guide 100 on a short distance. Beyond this short distance with a high flexibility, the guide 100 may recover a mild and constant flexibility to be able to push the stent (6).

Figure 3C:
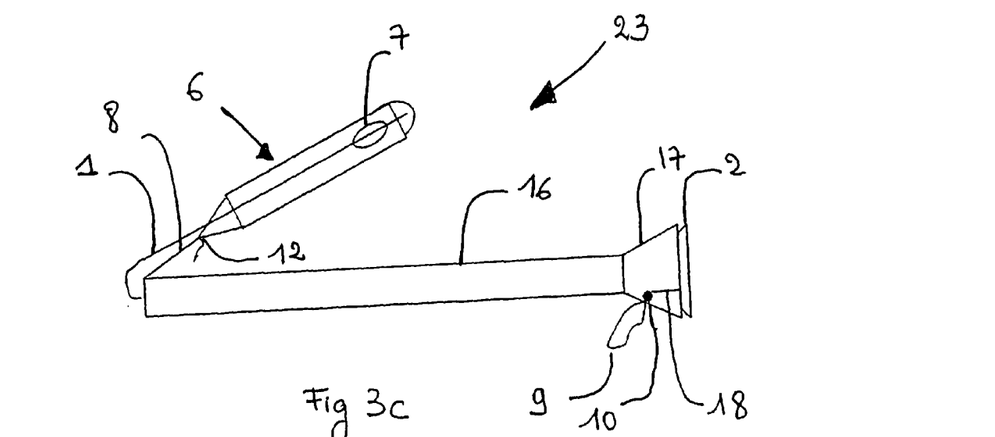
FIG. 3c shows schematically the device according to FIG. 3b in a "bent state".

Furthermore, as shown in FIG. 3c, the guide 100 according to the invention can be bent to an angle of 90° or more from a straight position at a point of the said guide 100 situated at a distal front end of a pusher tube 16, once the guide 100 has been inserted into the pusher tube 16. The flexibility of the guide 100 can be especially high as it emerges from the pusher tube 16 to facilitate the bending on a short distance, about one centimeter measured from the distal front end of the pusher tube 16.

As shown in FIG. 1a, the guide 1 can be a guide wire 3 which is made longitudinally rigid by a central steel core, said guide wire 3 having at its proximal end a means of abutment 2. The diameter of the wire is preferably lower than 1 mm. A small value of the diameter contributes to the flexibility of the distal tip of the guide 1, 100. Thus, the guide wire 3 provides an ideal compromise between small diameter, flexibility, and longitudinal stiffness to transmit the longitudinal force to insert the stent 6. Moreover, a small diameter reduces the contact surface between the guide 1, 100 and the inner surface 14 of the stent 6. This diminishes the friction forces between the guide 1, 100 and the stent 6 during the retrieval of the guide 1, 100. Thus, the risk of backwards displacement of the stent 6 is minimized during this manipulation.

As shown in FIG. 1c, the guide 100 can include at its distal tip a protective means 5 having a spherical shape, which acts as a protective means during the removal and/or the insertion of the guide 100.

According to other embodiments of the invention, the guide 1, 100 can be composed of at least two different zones having different lateral flexibility.

As shown in FIG. 1b to 1d, the guide 100 comprises a rod 4 having a proximal end which comprises a means of abutment 2. The rod 4 comprises a distal end which is connected to a guide wire 3. The diameter of the rod 4 is such that it allows the easy gliding of the rod 4 inside the pusher tube 16. The rod 4 can be rigid or slightly flexible so that it does not kink inside the pusher tube 16. The length of the rod 4 is such that, once the guide 100 has been inserted into the pusher tube 16, its distal part does not protrude outside of the distal orifice (front end) of the pusher tube 16 and its means of abutment 2 is in contact with the proximal end of the pusher tube 17, as it is shown in FIG. 3b. In this embodiment, the length of the guide wire 3 corresponds to the length of the stent 6 plus the length of the obstacle, such as a sphincter 21. Furthermore, as shown in FIG. 1d, the flexibility of the guide 100 can be particularly high at its connection with the rod 4, to facilitate the bending of an angle of 90° or more on a short distance, about one centimeter measured from the said connection to the rod 4. Beyond this short distance with a high flexibility, the guide 100 can have a mild and constant flexibility to be able to push the stent 6 without kinking inside.

Furthermore, the distal tip of the guide 1, 100 is bare and sharp. Indeed, any passage of the distal tip of the said guide 1, 100 through one of the orifices 7 laterally positioned at the distal tip of the stent 6 to drain a liquid (for example urine in the case of an endo-urethra stent) would lead to the injury of the canal in which the stent 6 is inserted.

Figure 4A:
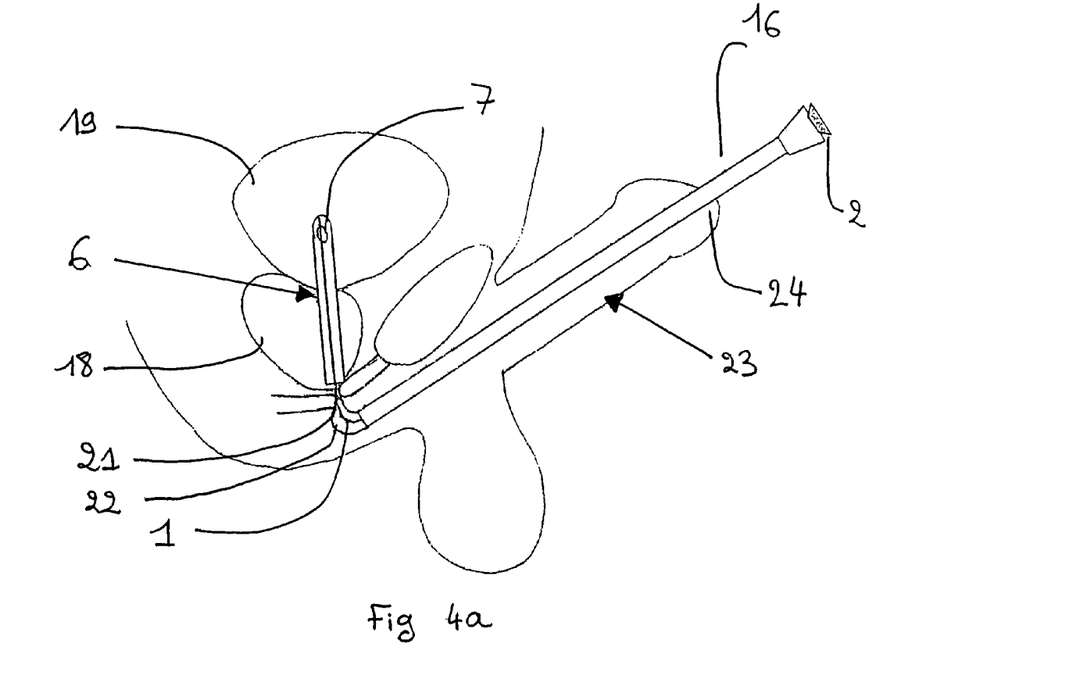
FIG. 4a shows schematically the inserted device.
Figure 4B:
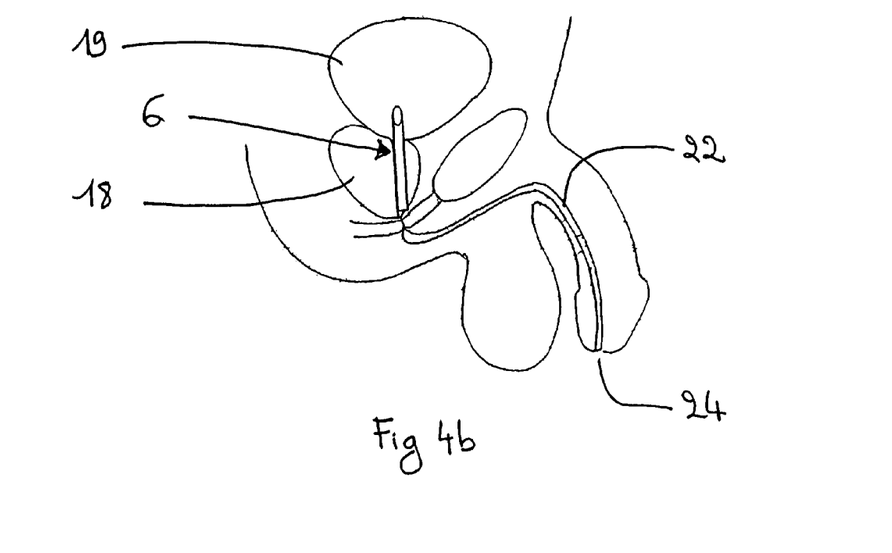
FIG. 4b shows schematically an inserted stent once the pusher tube and the guide have been removed.

During the insertion of the device 23 according to the invention, the guide 1 transmits to the distal tip of the stent 6 a longitudinal external force which is applied to the pusher tube 16 by the operator, so that the stent 6 passes through the obstacle (for example a sphincter 21) and, further, is placed in correct position at the level of a target organ, such as the bladder 19 as shown in FIGS. 4a and 4b. Furthermore, after the insertion of the stent 6 the guide 1 is carefully and smoothly retrieved from the tip of the stent 6 along the lumen of the stent 6 with minimal friction and further outside the stent 6 so that the stent 6 is not pulled backwards and remains in correct position.

Thus, during these steps of insertion and retrieval, any passage of the guide 1 through one of the orifice 7 of the stent 6 should be avoided. For this reason, the form of the distal tip of the guide 1 is bare and sharp and the distal tip of the stent 6 is designed allowing the safe lodgment of the tip of the guide 1 inside the lumen of the tip of the stent 6.

Figure 2A:
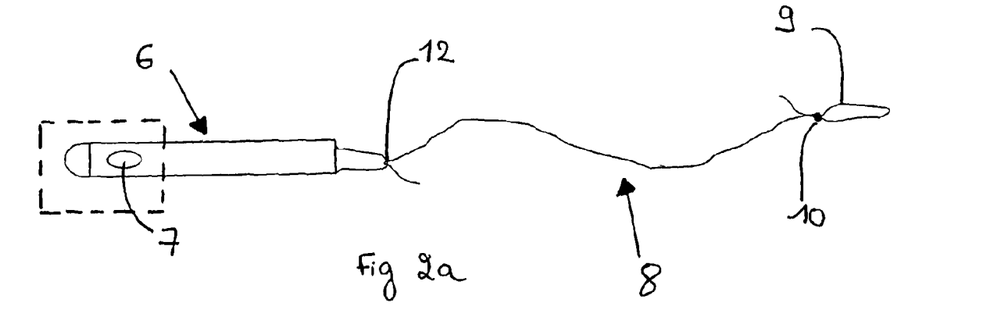
FIG. 2a shows in a schematically manner a stent according to the present invention with a thread.
Figure 2B:
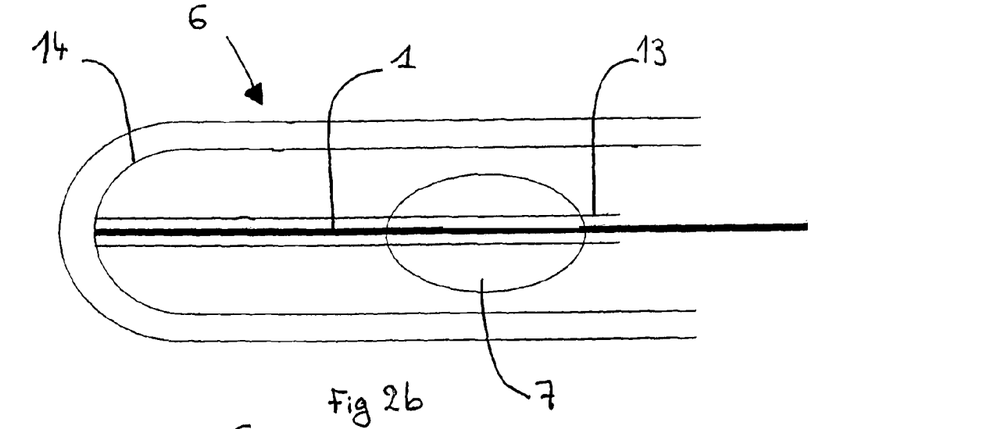
FIG. 2b is a partial enlarged view of the dotted box of FIG. 2a showing a distal tip of a stent according to the invention in an embodiment of the invention.

For this purpose, in one embodiment of the invention, as shown in FIG. 2*b*, the stent 6 includes a longitudinal thin sheath 13 which extends from the distal tip of the stent 6 to rearwards the orifice 7, for example 5 millimeter rearwards the said orifices 7, and which is in a preferred embodiment centered inside the said stent 6 so that the distal tip of the guide 1 is inserted into the said sheath 13 and its passage through the orifices 7 of the tip of the stent 6 is avoided.

Figure 2C:
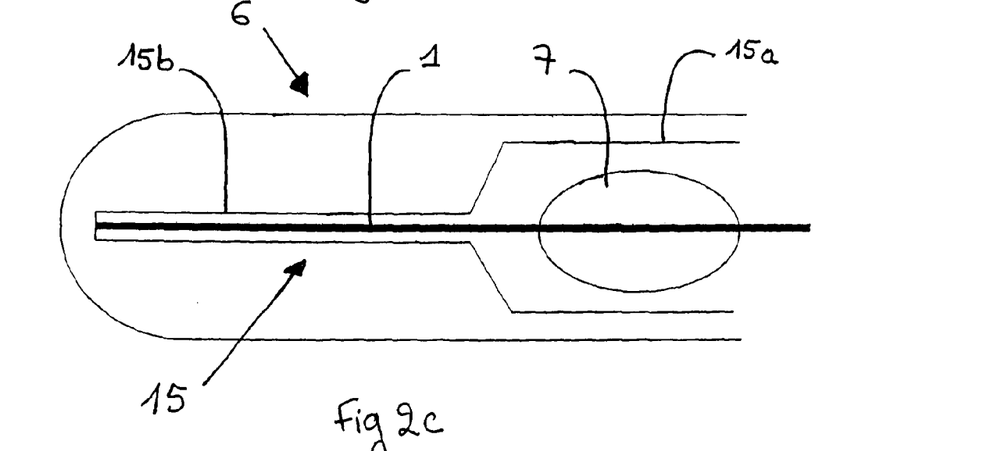
FIG. 2c is a partial enlarged view of the dotted box of FIG. 2a showing a distal tip of a stent according to the invention in another embodiment of the invention.

In another embodiment of the invention, as shown in FIG. 2*c*, the tip of the stent 6 is massive and comprises a channel 15 having a proximal part 15*a* prolongated by a distal part 15*b*, said orifice 7 being localized laterally in the proximal part 15*a*, so that the guide 1 can be inserted into the said distal part 15*b*.

The sheath 13 or the distal part 15*b* of the channel 15 has a diameter just above the diameter of the distal tip of the guide 1.

The flexibility of the stent 6 in which the guide 1, 100 is inserted is such that it allows a smooth insertion of the stent 6 through the obstacle, such as the striated sphincter 21. The force to apply for the insertion of the stent 6 should be quite similar to the one used for the insertion of a regular Foley catheter.

Among the variety of embodiments of stents 6 which can be used according to the invention, the mono-tubular embodiment of an endo-urethral stent is more precisely described.

In this embodiment, the outer diameter can have a value 22F Charrière (international unit used in the technical field of urology for the stents), which corresponds to the diameter of the male urethra 22. The inner diameter can be as large as possible provided the tube of the stent 6 does not kink and the lumen of the stent 6 is not occluded by the bending of the stent 6 inside the curved prostatic urethra of a prostate 20 with benign hypertrophy. The length can have a value of about 75 mm which allows the catheterization of the majority of the prostates with a total volume of up to 100 ml. The outer surface of the stent 6 may be smooth or helicoidal or having an accordion pleated shape. The surface can be reinforced by a metallic or a nylon spiral, said spiral being covered by a sleeve in a preferred embodiment. The proximal end of this stent 6 may have a straight section or half-Malecot design. The distal tip of this stent 6 may be blind and may comprise two orifices 7 positioned laterally at a distance of at least 1 cm past the said tip of the stent 6.

The pusher tube 16 has a longitudinal and lateral stiffness such that it does not kink inside the natural canal (which can be the male urethra 22) in which the stent 6 has to be inserted.

The pusher tube 16 can have an outer diameter which fits to the average inner diameter of the natural canal in which the stent 6 has to be inserted. In one embodiment of the invention, the said outer diameter is equivalent to the outer diameter of the stent 6.

For example, in the case of an endo-urethral stent, the outer diameter can have a value of 22F Charrière.

The inner diameter of the pusher tube 16 has a value allowing the insertion of the guide 1, 100 into the said pusher tube 16. If the guide 100 includes a rod 4, the inner diameter of the pusher tube 16 is such that the said rod 4 can be inserted into the pusher tube 16.

In the case of the insertion of an endo-urethral stent 6, the length of the pusher tube 16 is adapted to the average length of the sum of the lengths of the penile portion and the bulbous portion of the male urethra 22. A length of about 5 to 10 centimer of the pusher tube 16 is left outside the urethral meatus 24, when the distal front end of the pusher tube 16 abuts against the posterior wall of the bulbous urethra just below the striated sphincter 21.

The proximal end 17 of the pusher tube 16 has a shape, so that the means of abutment 2 of the guide 1, 100 can contact with the said proximal end 17 of the pusher tube 16, once the guide 1, 100 has been inserted into the pusher tube 16. In one embodiment of the invention, the proximal end 17 of the pusher tube 16 may extend in a shape of a cone. As shown in FIG. 3*a*, at least one slit 18 can be managed on the proximal end 17 of the pusher tube 16 to allow the locking of a knot 10 located at the proximal end of a thread 8 having a distal end attached to the stent 6.

The distal front end of the pusher tube 16 can be straight, but with a smooth edge to prevent any injury of the mucosa of the natural canal in which the stent 6 is inserted.

The outer surface of the pusher tube 16 is smooth. A centimetric scale can be printed on this surface with the value of "zero" at the level of the proximal end 17 of the pusher tube 16. More precisely, in the case of the insertion of an endo-urethral stent, the scale allows the measurement of the length of the pusher tube 16 left outside the urethral meatus 24, once the distal front end of the pusher tube 16 abuts against the posterior wall of the bulbous urethra below the striated sphincter 21.

The ratio between the outer diameter of the pusher tube 16 and the diameter of the flexible part of the guide 1, 100, which can be a guide wire 3 in an embodiment of the invention, is in the range of 1 to 10. In a preferred embodiment of the invention, the diameter of the guide wire 3 is lower than 1 mm diameter, and the outer diameter of the pusher tube 16 has a value of 8 mm diameter.

As shown in FIG. 2*a*, a thread 8 forming at its proximal end a loop 9 secured by a knot 10 is connected to the proximal end of a stent 6. The proximal end of the stent 6 has two opposite orifices not shown in FIG. 2*a*. Thus, the free distal end of the thread 8 is inserted through the two orifices and then is secured by a knot 12, so as to correctly attach the thread 8 to the proximal end of the stent 6. As shown in FIG. 3*a*, the thread 8 is inserted into the pusher tube 16 and locked by the insertion of the knot 10 of the loop 9 in the slit 18 of the proximal end 17 of the pusher tube 16.

As shown in FIG. 3*b*, the length of the thread 8 is such the thread 8 is blocked in the slit 18 in a stretched position when the guide 100 is inserted into the pusher tube 16 so that the means of abutment 2 is in contact with the proximal end 17 of the pusher tube 16 and the distal tip of the guide 100 is in contact with the distal tip of the stent 6.

The said thread 8 is blocked in a stretched position, and preferably centered if the connection to the proximal end of the stent 6 of the said thread 8 is centered.

FIG. 3*c* shows the device 23 according to FIG. 3*b* in a "bent state".

In an embodiment of the invention, the loop of the thread 8 secured by the knot 12 is long enough so that the knot 12 stays below the sphincter 21. Thus, the loop or the knot 12 can be identified in the bulbous urethra and can be grasped using a forceps under endoscopic control so that the stent 6 can be removed by pulling on the thread 8.

The tension of the thread 8 ensures the stability and the safety of the assembly of the three components of the device 23, which are a stent 6, a guide 1, 100 and a pusher tube 16, during the carrying out of the assembly and during the insertion of the said stent 6 into a natural canal such as a male urethra 22.

Thanks to the stretched thread 8, the device 23 keeps the same total length during the insertion of the stent 6. It prevents the guide 1, 100 from kinking at the level of the portion between the proximal end of the stent 6 and the distal front end of the pusher tube 16 and inside the stent 6. Indeed, any shortening of the total length of the device 23 could result in the dislodgement of the tip of the guide 1, 100 inside the distal tip of the stent 6. Moreover, any shortening of the total length of the device 23 could impair correct positioning of the stent 6 versus the obstacle such as the striated sphincter 21.

Furthermore, the contact of the tip of the guide 1, 100 with the tip of the stent 6 has preferably to be loose for facilitating the retrieval of the said guide 1, 100 out of the stent 6 without any displacement of the stent 6 from its correct position. In the absence of the tension of the thread 8, the stent 6 could be dropped out of the tip of the guide 1, 100.

Moreover, during the insertion of the stent 6, any retrieval movement applied by the operator to the pusher tube 16 could dislodge the tip of the guide 1, 100 from its protective means (the sheath 13 or the channel 15 at the distal tip of the stent 6) and lead to the injury of the natural canal such as the male urethra 22.

The thread 8 can be made of a monofilament polypropylene suture having a size of 0000 (international unit used for surgical suture).

The length of the thread 8 measured between the attachment to the proximal end of the stent 6 and the knot 10 at the proximal end of the said thread 8 is such that once the guide 1, 100, the stent 6 and the pusher tube 16 have been assembled, the thread 8 moves from a loose state to a stretched state. The tip of the guide 1, 100 pushes forward the distal tip of the stent 6 which results in the tension of the thread 8. As it leaves the stent 6 the stretched thread 8 is parallel to the guide 1, 100 before it engages through the distal front end of the pusher tube 16.

To carry out the assembly of the device 23 according to the present invention, the thread 8 which is attached to the proximal end of the stent 6, is inserted through the lumen of the pusher tube 16 starting from its distal front end in the direction of its proximal end 17 and the knot 10 securing the loop 9 at the proximal end of the thread 8 is blocked in the slit 18 of the proximal end of the pusher tube 17.

As shown in FIG. 3a, the guide 100 is inserted through the pusher tube 16; as it emerges from the distal front end of the pusher tube 16, then, the guide 100 is inserted through the stent 6 so that to contact with its distal tip the distal tip of the stent 6.

The guide 100 is locked to the pusher tube 16 thanks to its means of abutment 2 with the proximal end 17 of the pusher tube 16. The thread 8 is stretched, once the device 23 comprising the stent 6 the guide 100 and the pusher tube 16 is correctly assembled, as it is shown in FIG. 3b. Furthermore, in a preferred embodiment of the invention, the distal tip of the guide 1 can be safely positioned thanks to a sheath 13 (FIG. 2b) or a channel 15 (FIG. 2c).

For the insertion of the device 23 into a natural canal in which a stent 6 has to be inserted, longitudinal force is applied to the pusher tube 16 by the operator which is transmitted to the guide 1, 100 inserted into the said pusher tube 16 and locked to by the means of abutment 2. The distal tip of the guide 1, 100 transmits the pushing force to the distal tip of the, stent 6 so that the said stent 6 is moved through the natural canal.

In the case of the insertion of an endo-urethral stent, the patient lies in the dorsal decubitus position. The urethra 22 is anesthetized and lubricated by the instillation of a gel through the urethral meatus 24. The operator stretches the penis upwards so that the mobile penile part of the urethra is in alignment with the fixed bulbous part of the urethra, as it is shown in FIG. 4a. While the operator maintains this alignment, the device 23 is inserted through the urethral meatus, said device comprising a stent 6, connected at its proximal end to a thread 8, a guide 1 having a portion of the length of the striated sphincter 21 which is neither inserted into the stent 6 nor into the pusher tube 16, and a pusher tube 16. During the progression of the device 23 along the lumen of the urethra 22, the operator will feel a first minor resistance due to the passage of the stent 6 through the striated sphincter 21 and the prostatic urethra, followed by a second significant resistance stopping progression, once the distal front end of the pusher tube 16 abuts against the posterior wall of the bulbous urethra just below the striated sphincter 21. At this point, the stent 6 is correctly positioned and the guide 1 and the pusher tube 16 can be removed, leaving the stent 6 in the prostatic urethra.

The operator can simulate the insertion of the device 23 using a replica of the pusher tube 16 but without the guide 1 or the stent 6. This allows the operator to calibrate the penile and bulbous portions of the urethra 22 and to feel the abutment of the distal front end of the pusher tube 16 against the posterior wall of the bulbous urethra just below the striated sphincter 21. The operator will learn from the tactile feed-back and note the length in centimeters of the pusher tube 16 left outside the urethral meatus 24. After removal of the replica and during the insertion of the device 23 according to the invention comprising a stent 6, a guide 1 and a pusher tube 16, the operator will have the same tactile feed-back completed by the visual control of the same length of the pusher tube 16 left outside the urethral meatus 24.

After the insertion of the device allowing correct positioning of the stent 6, the guide 1 is disconnected and removed from the pusher tube 16; the knot 10 at the proximal end of the thread 8 is disengaged from the slit of the proximal end 17 of the pusher tube 16.

The pusher tube 16 is removed. The operator does not feel any resistance during retrieval of the guide 1 thanks to its thin diameter and its flexibility. Furthermore, the sharp tip of the guide 1 cannot hook one of the orifices 7 of the stent 6 and the loop of thread 8 attached to the proximal end of the stent 6. Thus there is no risk of backwards displacement of the stent 6 during retrieval of the guide 1.

The thread 8 is cut as it emerges from the urethral meatus 24. The thread 8 is not shown on FIG. 4b which is a schema of an inserted stent according to the present invention in a male bladder 19.

Furthermore, it is important that the inner diameter of the pusher tube 16 is such that the passage of both the thread 8 and the rod 4 of the guide 1, 100 is loose enough in such a way that the retrieval of the guide 1, 100 out of the pusher tube 16 will not pull the thread 8 and displace the stent 6 backwards out of its correct position.

While preferred embodiments have been shown and described, various modifications and substitutions may be made thereto without departing from the spirit and scope of the invention. Accordingly, it is to be understood that the present invention has been described by way of illustration and not limitations.

The invention claimed is:

1. A device, comprising:
a guide configured to push a stent through a lumen of a natural canal; and
a stent, the stent comprising a lateral wall having at least one orifice,
wherein the guide comprises at least one flexible part having:
a predetermined longitudinal stiffness such that the guide does not kink by pushing the stent along the lumen and
a lateral flexibility that allows a reversible deformation of the at least one flexible part from a straight position to a bent position so:
as to follow the curve of the natural canal under an application of minimal external forces exerted by an operator such that the stent does not cause any injury in the natural canal, and
a deformation of the guide by a change in a direction following a passage through an obstacle creates an increasing of a resistance to progression of the guide inside the lumen of the natural canal which is felt by an operator and so the progression of the guide cannot continue unless the operator applies to the device a force that will more deform the canal;
wherein the guide comprises at least one straight and rigid proximal rod prolongated by the at least one flexible part, and a segment of the at least one flexible part which is closest to the straight and rigid proximal rod has a highest flexibility of the at least one flexible part,
a portion of the guide at a location on a side of the at least one flexible part that is opposite from the straight and rigid proximal rod is configured to be insertable into the stent, by virtue of an internal housing of the stent in which the guide can be inserted,
the guide is a continuous member,
the guide includes a distal tip,
the guide is configured to be insertable into a pusher tube so that an abutment of the guide is in contact with a proximal end of the pusher tube,
an outer diameter of the guide is non-constant, with an outer diameter of the straight and rigid proximal rod being larger than an outer diameter of the at least one flexible part, the outer diameter of the guide having an abrupt decrease from the straight and rigid proximal rod to the at least one flexible part.

2. The device according to claim 1, wherein the guide further comprises a proximal end comprising the abutment.

3. The device according to claim 1, wherein the at least one flexible part is a guide wire.

4. The device according to claim 1, wherein the guide has a predetermined longitudinal stiffness that allows the guide to push an endo-urethral stent along the male urethra.

5. The device according to claim 1, wherein the a distal tip of the guide comprises a protector.

6. The device according to claim 1,
wherein the stent includes a longitudinal sheath, which extends from a distal tip of the stent to rearward of the orifice, so that the distal tip of the guide can be inserted into the sheath.

7. The device according to claim 1,
wherein the stent includes a massive distal tip and comprising a channel having a proximal part prolongated by a distal part, whose section is smaller than the section of the proximal part, said orifice being localized laterally in the proximal part, so that the distal tip of the guide can be inserted into the distal part.

8. The device according to claim 1, wherein the stent is an endo-urethral stent.

9. The device according to claim 1, wherein the stent has a blind distal tip.

10. The device according to claim 1, further comprising:
the pusher tube, the pusher tube including a proximal end, which comprises a connector, and
a thread having a proximal end, which is blocked in the connector, said thread having a length such that the thread is blocked in a stretched position when the guide is correctly inserted into the pusher tube and the distal tip of the guide is in contact with the distal tip of the stent.

11. The device according to claim 10, wherein the connector is a slit.

12. The device according to claim 10, wherein a ratio between the outer diameter of the at least one flexible part and an outer diameter of the pusher tube is 1:10.

13. A therapeutic method for positioning a stent at the level of a target organ comprising passing a device according to claim 1 through an obstacle.

14. The device according to claim 1, wherein the obstacle is a sphincter.

15. The device according to claim 1, wherein the distal tip of the guide is sharp.

16. The device according to claim 1, further comprising a second abutment adapted to allow for correct positioning of the stent by virtue of abutment of the guide against a posterior wall of a bulbous urethra, the second abutment being disposed at a junction between a distal end of the straight and rigid proximal rod and the at least one flexible part.

17. The device according to claim 1, wherein a segment of the at least one flexible part having a highest flexibility of the at least one flexible part has a thinner diameter than other segments of the at least one flexible part.

* * * * *